United States Patent [19]

Lukacovic

[11] Patent Number: 5,622,689

[45] Date of Patent: *Apr. 22, 1997

[54] ORAL COMPOSITIONS

[75] Inventor: Michael F. Lukacovic, West Chester, Ohio

[73] Assignee: The Procter & Gamble Company, Cincinnati, Ohio

[*] Notice: The term of this patent shall not extend beyond the expiration date of Pat. No. 5,620,679.

[21] Appl. No.: 485,224

[22] Filed: Jun. 7, 1995

Related U.S. Application Data

[62] Division of Ser. No. 242,491, May 13, 1994, Pat. No. 5,560,905.

[51] Int. Cl.$^6$ .............................. A61K 7/16; A61K 7/18; A61K 7/28
[52] U.S. Cl. ................... 424/52; 424/49; 424/50
[58] Field of Search ........................... 424/49–58

[56] References Cited

U.S. PATENT DOCUMENTS

| | | | |
|---|---|---|---|
| 2,876,167 | 3/1959 | Manahan | 424/52 |
| 3,696,191 | 10/1972 | Weeks | 424/50 |
| 3,897,548 | 7/1975 | Katz | 424/54 |
| 3,957,967 | 5/1976 | L'Orange | 424/48 |
| 3,991,177 | 11/1976 | Vidra et al. | 424/50 |
| 4,025,616 | 5/1977 | Haefele | 424/52 |
| 4,058,595 | 11/1977 | Colodney | 424/50 |
| 4,080,440 | 3/1978 | DiGuilio et al. | 424/49 |
| 4,115,546 | 9/1978 | Vidra et al. | 424/50 |
| 4,138,476 | 2/1979 | Simonson et al. | 424/50 |
| 4,138,477 | 2/1979 | Gaffar | 424/52 |
| 4,140,758 | 2/1979 | Vidra et al. | 424/50 |
| 4,154,815 | 5/1979 | Pader | 424/50 |
| 4,183,914 | 1/1980 | Gaffar et al. | 424/48 |
| 4,259,316 | 3/1981 | Nakashima et al. | 424/52 |
| 4,332,791 | 6/1982 | Raaf et al. | 424/52 |
| 4,335,102 | 6/1982 | Nakashima et al. | 424/52 |
| 4,339,429 | 7/1982 | Raaf et al. | 424/49 |
| 4,363,794 | 12/1982 | Ochiai et al. | 424/52 |
| 4,487,757 | 12/1984 | Kiozpeoplou | 424/49 |
| 4,652,444 | 3/1987 | Maurer | 424/49 |
| 4,708,864 | 11/1987 | Maurer | 424/49 |
| 4,725,428 | 2/1988 | Miyahara et al. | 424/50 |
| 4,737,359 | 4/1988 | Eigen et al. | 424/50 |
| 4,749,562 | 6/1988 | Lane et al. | 424/49 |
| 4,842,847 | 6/1989 | Amjad | 424/52 |
| 4,902,497 | 2/1990 | Crisanti et al. | 424/52 |
| 4,950,479 | 8/1990 | Hill et al. | 424/49 |
| 4,986,981 | 1/1991 | Glace et al. | 424/50 |
| 4,992,420 | 2/1991 | Neeser | 514/8 |
| 4,996,042 | 2/1991 | Wagner | 424/54 |
| 5,000,939 | 3/1991 | Dring et al. | 424/48 |
| 5,028,412 | 7/1991 | Putt et al. | 424/48 |
| 5,032,387 | 7/1991 | Hill et al. | 424/49 |
| 5,094,840 | 3/1992 | Isobe et al. | 424/50 |
| 5,109,127 | 4/1992 | Sekiguchi et al. | 536/115 |
| 5,143,720 | 9/1992 | Lopes | 424/55 |
| 5,145,666 | 9/1992 | Lukacovic et al. | 424/52 |
| 5,180,577 | 1/1993 | Polefka et al. | 424/52 |
| 5,190,747 | 3/1993 | Sekiguchi et al. | 424/56 |
| 5,192,533 | 3/1993 | Elliott et al. | 424/54 |
| 5,244,593 | 9/1993 | Roselle et al. | 252/99 |
| 5,258,304 | 11/1993 | Carpenter et al. | 435/264 |
| 5,280,042 | 1/1994 | Lopes | 424/49 |
| 5,281,410 | 1/1994 | Lukacovic et al. | 424/52 |
| 5,286,479 | 2/1994 | Garlich et al. | 424/54 |
| 5,320,830 | 6/1994 | Lukacovic et al. | 424/52 |
| 5,320,831 | 6/1994 | Majeti et al. | 424/52 |
| 5,431,903 | 7/1995 | Majeti et al. | 424/52 |
| 5,437,856 | 8/1995 | Lukacovic et al. | 424/50 |

FOREIGN PATENT DOCUMENTS

| | | | |
|---|---|---|---|
| 190762 | 8/1986 | European Pat. Off. | A61K 7/61 |
| 265186 | 4/1988 | European Pat. Off. | A61K 7/16 |
| 427175 | 5/1991 | European Pat. Off. | A61K 7/16 |
| 55-069508 | 5/1980 | Japan | A61K 7/16 |
| 61036211A | 2/1986 | Japan | A61K 7/16 |
| 02105898A | 4/1990 | Japan | C11D 3/38 |
| 03223209A | 10/1990 | Japan | A61K 7/28 |
| 03128313A | 5/1991 | Japan | A61K 7/16 |
| WO86/02831 | 5/1986 | WIPO | A61K 7/18 |
| WO9367851 | 4/1993 | WIPO | A61K 7/16 |

*Primary Examiner*—Shep K. Rose
*Attorney, Agent, or Firm*—David K. Dabbiere; Douglas C. Mohl; Jacobus C. Rasser

[57] ABSTRACT

Oral compositions, such as oral gels, toothpastes and mouthwashes, containing a tartaric acid chelating agent and a hydrophobic anionic surfactant.

11 Claims, No Drawings

ORAL COMPOSITIONS

This is a division of application Ser. No. 08/242,491, filed on May 13, 1994, now U.S. Pat. No. 5,560,905.

TECHNICAL FIELD

The present invention relates to oral compositions containing a tartaric acid chelating agent and a hydrophobic anionic surfactant in a suitable oral carrier.

BACKGROUND OF THE INVENTION

The formation of dental plaque is the primary source of dental caries, gingival and periodontal disease and tooth loss. Dental plaque is a mixed matrix of bacteria, epithelial cells, leukocytes, macrophages and other oral exudate. Bacteria comprise approximately three-quarters of the plaque matrix. Any given sample of dental plaque could contain as many a 400 different varieties of microorganisms. This mix includes both aerobic and anaerobic bacteria, fungi and protozoa. Viruses have also been found in samples of dental plaque.

This matrix of organisms and oral exudate continues expanding and coalesces with other plaque growths situated nearby. The bacteria synthesize levans and glucans from sucrose found in the oral cavity providing energy for the microorganisms. These glucans, levans and microorganisms form an adhesive skeleton for the continued proliferation of plaque.

Calculus is a yellow or white mineralized deposit of bacterial plaque. Inorganic in nature, calculus consists primarily of calcium and magnesium phosphate and calcium carbonate. Calculus forms in layers as does plaque and is simply the mineralization of plaque's layered bacteria. Calculus is formed when plaque's protein-carbohydrate matrix accumulates calcium followed by the precipitation and mineralization of crystalline calcium phosphate. Once mineralized calculus is formed, another layer of bacteria adheres to the surface forming yet another layer of plaque which is subsequently mineralized into calculus.

The failure to retard or stop the proliferation of plaque is detrimental to oral health. Plaque formation leads to dental caries, gingival inflammation, periodontal disease and ultimately tooth loss. The present inventors recognize these problems and have developed a composition suitable for combating oral disease, preventing tooth loss, and leading to general oral well-being.

The use of a variety of agents to clean the oral cavity and reduce plaque and mouth malodor has been recognized for some time. Examples include: U.S. Pat. No. 3,696,191, Oct. 3, 1972 to Weeks; U.S. Pat. No. 3,991,177, Nov. 9, 1976 to Vidra et al.; U.S. Pat. No. 4,058,595, Nov. 15, 1977 to Colodney; U.S. Pat. No. 4,115,546, to Vidra et al.; U.S. Pat. No. 4,138,476, Feb. 6, 1979 to Simonson et al.; U.S. Pat. No. 4,140,758, Feb. 20, 1979 to Vidra et al.; U.S. Pat. No. 4,154,815, May 15, 1979 to Pader; U.S. Pat. No. 4,737,359, Apr. 12, 1988 to Eigen et al.; U.S. Pat. No. 4,986,981, Jan. 22, 1991 to Glace et al.; U.S. Pat. No. 4,992,420, Feb. 12, 1991 to Nesser; U.S. Pat. No. 5,000,939, Mar. 19, 1991 to Dring et al.; Kokai 02/105,898, published Apr. 18, 1990 to Kao Corporation; Kokai 03/128,313, published May 31, 1991 to Nippon Kotai Kenkyu and Kokai 03/223,209, published Oct. 2, 1991 to Lion Corporation; U.S. Pat. No. 4,652,444, Mar 24, 1987 to Maurer; U.S. Pat. No. 4,725,428, Feb. 16, 1988 to Miyahara et al.; U.S. Pat. No. 4,355,022, Oct. 19, 1982 to Rabussay and PCT application WO 86/02831, published May 22, 1986 to Zetachron, Inc.

While compositions containing a sarcosinate, isethionate, and/or taurate surfactant along with a chelating agent are known, see, for example U.S. Pat. No. 5,258,304, Nov. 2, 1993 to Carpenter et al., U.S. Pat. No. 5,244,593, Sep. 14, 1993 to Roselle et al., U.S. Pat. No. 4,339,429, Jul. 13, 1982 to Raaf et al., U.S. Pat. No. 3,957,967, May 18, 1976 to L'Orange, and U.S. Pat. No. 4,332,791, Jun. 1, 1982 to Raaf et al. None of these references teach or suggest the oral compositions of the present invention with specific levels of the surfactant component and tartrate chelating agent and which are substantially free of copper, iron and zinc ions which would interfere with the ability of the tartrate chelant to bind calcium in plaque and thereby inhibit the compositions efficacy.

The present inventor has discovered that the compositions of the present invention containing specific levels of a tartaric acid chelating agent in combination with a surfactant selected from sarcosinate surfactants, isethionate surfactants and taurate surfactants provide superior cleaning and abate the formation of plaque and calculus without undue desquamation of oral soft tissue.

It is therefore an object of the present invention to provide an oral care product and methods of using the same that are effective in arresting the accumulation of plaque and preventing gingivitis without undue desquamation. It is a further object of the present invention to provide such compositions and methods that will also abate subsequent calculus formation without undue desquamation. It is still a further object of the present invention to provide compositions that will clean the oral cavity and provide improved methods of promoting vitality of the oral cavity.

These objectives and additional objectives will become readily apparent from the detailed description which follows.

SUMMARY OF THE INVENTION

The present invention relates to oral compositions which provide antiplaque, antigingivitis, and anticalculus benefits with improved oral cleaning properties with reduced desquamation, comprising:
  a. from about 0.1% to about 2.5% of a surfactant selected from the group consisting of sarcosinate surfactants, isethionate surfactants and tautate suffactants; and
  b. from about 0.1 to about 2.5% of tartaric acid or a pharmaceutically-acceptable acid salt thereof wherein the level of a. and b. does not exceed 4.0% and preferably does not exceed 3.5% by weight of the total composition and further wherein said composition is substantially free of copper, iron and zinc ions.

The present invention further relates to a method of reducing plaque, gingivitis and calculus using the above compositions.

All percentages and ratios herein are by weight unless otherwise specified. Additionally, all measurements are made at 25° C. unless otherwise specified.

DETAILED DESCRIPTION OF THE INVENTION

By "safe and effective amount," as used herein, means a sufficient amount to reduce plaque/gingivitis without harming the tissues and structures of the oral cavity.

By the term "suitable oral carrier," as used herein, means a suitable vehicle which can be used to apply the present compositions to the oral cavity in a safe and effective manner.

By "substantially free of copper, iron and zinc ions" as used herein, means that the compositions contain a level wherein said ions will not complex with the chelating agent sufficient to inhibit its activity. This level is generally less than about 0.3%, preferably less than about 0.1% and most preferably less than about 0.05% of copper, iron and zinc ions.

The pH of the present herein described compositions range from about 4.0 to about 9.5, with the preferred pH being from about 5.0 to about 9.0 and the most preferred pH being 6.5 to about 9.0.

The essential as well as optional components of the compositions of the present invention are described in the following paragraphs.

Surfactants

One of the essential agents required by the present invention is a surfactant selected from the group consisting of sarcosinate surfactants, isethionate surfactants and taurate surfactants. Preferred for use herein are alkali metal or ammonium salts of these surfactants. Most preferred herein are the sodium and potassium salts of the following: lauroyl sarcosinate, myristoyl sarcosinate, palmitoyl sarcosinate, stearoyl sarcosinate and oleoyl sarcosinate.

This surfactant can be present in the compositions of the present invention from about 0.1% to about 2.5%, preferably from about 0.3% to about 2.5% and most preferably from about 0.5% to about 2.0% by weight of the total composition.

Other suitable compatible surfactants can optionally be used along with the sarcosinate surfactant in the compositions of the present invention. Suitable optional surfactants are described more fully in U.S. Pat. No. 3,959,458, May 25, 1976 to Agdcola et at.; U.S. Pat. No. 3,959,458, Feb. 10, 1976 to Haefele; and U.S. Pat. No. 4,051,234, Sep. 27, 1988 to Gieske et at. These patents are incorporated herein by reference.

Preferred anionic surfactants useful herein include the water-soluble salts of alkyl sulfates having from 10 to 18 carbon atoms in the alkyl radical and the water-soluble salts of sulfonated monoglycerides of fatty acids having from 10 to 18 carbon atoms. Sodium lauryl sulfate and sodium coconut monoglyceride sulfonates are examples of anionic surfactants of this type. Mixtures of anionic surfactants can also be utilized.

Preferred cationic surfactants useful in the present invention can be broadly defined as derivatives of aliphatic quaternary ammonium compounds having one long alkyl chain containing from about 8 to 18 carbon atoms such as lauryl trimethylamonium chloride; cetyl pyridinium chloride; cetyl trimethylammonium bromide; di-is-obutylphenoxyethyi-dimethylbenzylammonium chloride; coconut alkyltrimethylammonium nitrite; cetyl pyridinium fluoride; etc. Preferred compounds are the quaternary ammonium fluorides described in U.S. Pat. No. 3,535,421, Oct. 20, 1970, to Briner et al., herein incorporated by reference, where said quaternary ammonium fluorides have detergent properties. Certain cationic surfactants can also act as germicides in the compositions disclosed herein. Cationic surfactants such as chlorhexadine, although suitable for use in the current invention, are not preferred due to their capacity to stain the oral cavity's hard tissues. Persons skilled in the art are aware of this possibility and should incorporate cationic surfactants only with this limitation in mind.

Preferred nonionic suffactants that can be used in the compositions of the present invention can be broadly defined as compounds produced by the condensation lion of alkylene oxide groups (hydrophilic in nature) with an organic hydrophobic compound which may be aliphatic or alkylaromatic in nature. Examples of suitable nonionic surfactants include the Pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials.

Preferred zwitterionic synthetic surfactants useful in the present invention can be broadly described as derivatives of aliphatic quaternary ammonium, phosphomium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate or phosphonate.

Preferred betaine surfactants are disclosed in U.S. Pat. No. 5,180,577 to Polefka et al., issued Jan. 19, 1993. Typical alkyl dimethyl betaines include decyl betaine or 2-(N-decyl-N,N-dimethylammonio) acetate, coco betaine or 2-(N-coc-N, N-dimethyl ammonio) acetate, myristyl betaine, palmityl betaine, lauryl betaine, cetyl betaine, cetyl betaine, stearyl betaine, etc. The amidobetaines are exemplified by cocoamidoethyl betaine, cocoamidopropyl betaine, lauramidopropyl betaine and the like. The betaines of choice are preferably the cocoarnidopropyl betaine and, more preferably, the lauramido propyl betaine.

Chelating agents

Another of the essential agents required by the present invention is a tartaric acid chelating agent or pharmaceutically-acceptable salt thereof. Chelating agents are able to complex calcium found in the cell walls of the bacteria. Binding of this calcium weakens the bacterial cell wall and augments bacterial lysis. Chelating agents can also disrupt plaque by removing calcium from the calcium bridges which help hold this biomass intact. However, it is possible to use a chelating agent which has an affinity for calcium that is too high. This results in tooth demineralization and is contrary to the objects and intentions of the present invention. The inventor has found the sarcosinate surfactant in combination with tartaric acid chelating agent provides improved cleaning with reduced plaque and calculus formation.

Preferred herein are alkali metal salts of tartaric acid. Most preferred for use herein are disodium tartrate, dipotassium tanrate, sodium potassium tartrate, sodium hydrogen tartrate and potassium hydrogen tartrate. The tartaric acid salt chelating agent can be used alone or in combination with other optional chelating agents.

Other optional chelating agents can be used along with the tartaric acid salt. Preferably these chelating agents have a calcium binding constant of about $10^1$ to $10^5$ provide improved cleaning with reduced plaque and calculus formation. One of the preferred chelating agents possessing a suitable calcium binding constant and therefore suitable for use in the instant invention is a citric acid/alkali metal citrate combination. The amounts of citric acid suitable for use in the present invention are about 0.1% to about 3.0%, preferably from about 0.5% to about 2.5% and more preferably from about 1.0% to about 2.5%. Sodium and potassium citrate are the preferred alkali metal citrates, with sodium citrate being the most preferred.

Another group of agents suitable for use as chelating agents in the present invention are the soluble pyrophosphates. The pyrophosphate salts used in the present compositions can be any of the alkali metal pyrophosphate salts. Specific salts include tetra alkali metal pyrophosphate, dialkali metal diacid pyrophosphate, trialkali metal monoacid pyrophosphate and mixtures thereof, wherein the alkali metals are preferably sodium or potassium. The salts are useful in both their hydrated and urthydrated forms. An effective amount of pyrophosphate salt useful in the present composition is generally enough to provide at least 1.0% pyrophosphate ion, preferably from about 1.5% to about 6%, more preferably from about 3.5% to about 6% of such ions. It is to be appreciated that the level of pyrophosphate ions is that capable of being provided to the composition (i.e., the theoretical amount at an appropriate pH) and that pyrophosphate forms other than $P_2O_7-4$ (e.g., $(HP_2O_7-3)$) may be present when a final product pH is established.

The pyrophosphate salts are described in more detail in Kirk & Othmer, *Encyclopedia of Chemical Technology*, Second Edition, Volume 15, Interscience Publishers (1968), incorporated herein by reference.

Still another possible group of chelating agents suitable for use in the present invention are the anionic polymeric polycarboxylates. Such materials are well known in the art, being employed in the form of their free acids or partially or preferably fully neutralized water soluble alkali metal (e.g. potassium and preferably sodium) or ammonium salts. Preferred are 1:4 to 4:1 copolymers of maleic arthydride or acid with another polymerizable ethylenically unsaturated toohomer, preferably methyl vinyl ether (methoxyethylene) having a molecular weight (M. W.) of about 30,000 to about 1,000,000. These copolymers are available for example as Gantrez AN 139 (M.W. 500,000), AN 119 (M.W. 250,000) and preferably S-97 Pharmaceutical Grade (M.W. 70,000), of GAF Chemicals Corporation.

Other operative polymeric polycarboxylates include those such as the 1:1 copolymers of maleic anhydride with ethyl acrylate, hydroxyethyl methacrylate, N-vinyl-2-pyrollidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone.

Additional operative polymeric polycarboxylates are disclosed in U.S. Pat. No. 4,138,477, Feb. 6, 1979 to Graffar and U.S. Pat. No. 4,138,914, Jan. 15, 1980 to Gaffar et al. both patents are incorporated herein by reference, and include copolymers of maleic arthydride with styrene, isobutylene or ethyl vinyl ether, polyacrylic, polyitaconic and polymaleic acids, and sulfoacrylic oligomers of M.W. as low as 1,000 available as Uniroyal ND-2.

In addition to the above described essential components, the embodiments of this invention can contain a variety of optional dentifrice ingredients some of which are described below. Optional ingredients include, for example, but are not limited to, adhesives, sudsing agents, flavoring agents, sweetening agents, additional antiplaque agents, abrasives, and coloring agents. These and other optional components are further described in U.S. Pat. No. 5,004,597, Apr. 2, 1991 to Majeti; U.S. Pat. No. 4,885,155, Dec. 5, 1989 to Parran, Jr. et al.; U.S. Pat. No. 3,959,458, May 25, 1976 to Agricola et al. and U.S. Pat. No. 3,937,807, Feb. 10, 1976 to Haefele, all being incorporated herein by reference.

PHARMACEUTICALLY ACCEPTABLE CARRIER

The carrier for the components of the present compositions can be any vehicle suitable for use in the oral cavity. Such carriers include the usual components of mouthwashes, toothpastes, tooth powders, prophylaxis pastes, lozenges, gums and the like and are more fully described hereinafter. Dentifrices and mouthwashes are the preferred systems.

The abrasive polishing material contemplated for use in the present invention can be any material which does not excessively abrade dentin and does not provide calcium ions which may precipitate with, for example, the fluoride ions provided from stannous fluoride. These include, for example, silicas including gels and precipitates, insoluble sodium polymetaphosphate, β-phase calcium pyrophosphate, hydrated alumina, and resinous abrasive materials such as particulate condensation products of urea and formaldehyde, and others such as disclosed by Cooley et al. in U.S. Pat. No. 3,070,510, Dec. 25, 1962, incorporated herein by reference. Mixtures of abrasives may also be used. Abrasives such as calcium carbonate, calcium phosphate and regular calcium pyrophosphate are not preferred for use in the present compositions since they provide calcium ions which can complex F-.

Silica dental abrasives, of various types, can provide the unique benefits of exceptional dental cleaning and polishing performance without unduly abrading tooth enamel or dentin. Silica abrasive materials are also exceptionally compatible with sources of soluble fluoride. For these reasons they are preferred for use herein.

The silica abrasive polishing materials useful herein, as well as the other abrasive, generally have an average particle size ranging between about 0.1 and 30 microns, preferably 5 and 15 microns. The silica abrasive can be precipitated silica or silica gels such as the silica xerogels described in Pader et al., U.S. Pat. No. 3,538,230, issued Mar. 2, 1970 and DiGiulio, U.S. Pat. No. 3,862,307, Jun. 21, 1975 both incorporated herein by reference. Preferred are the silica xerogels marketed under the tradename "Syloid" by the W. R. Grace & Company, Davison Chemical Division. Preferred precipitated silica materials include those marketed by the J. M. Huber Corporation under the tradename, "Zeodent", particularly the silica carrying the designation "Zeodent 119". These silica abrasives are described in U.S. Pat. No. 4,340,583, Jul. 29, 1982, incorporated herein by reference.

The abrasive in the compositions described herein is present at a level of from about 6% to about 70%, preferably from about 15% to about 35% when the dentifrice is a toothpaste. Higher levels, as high as 95%, may be used if the composition is a toothpowder.

Flavoring agents can also be added to dentifrice compositions. Suitable flavoring agents include oil of wintergreen, oil of peppermint, oil of spearmint, oil of sassafras, and oil of clove. Sweetening agents which can be used include aspartame, acesulfame, saccharin, dextrose, levulose and sodium cyclamate. Flavoring and sweetening agents are generally used in dentifrices at levels of from about 0.005% to about 2% by weight.

Dentifrice compositions can also contain emulsifying agents. Suitable emulsifying agents are those which are reasonably stable and foam throughout a wide pH range, including non-soap anionic, nonionic, cationic, zwitterionic and amphoteric organic synthetic detergents. Many of these suitable suffactants are disclosed by Gieske et al, in U.S. Pat. No. 4,051,234, Sep. 27, 1977, incorporated herein by reference.

It is common to have an additional water-soluble fluoride compound present in dentifrices and other oral compositions in an amount sufficient to give a fluoride ion concentration in the composition at 25° C., and/or when it is used of from about 0.0025% to about 5.0% by weight, preferably from about 0.005% to about 2.0% by weight, to provide additional anticaries effectiveness. A wide variety of fluoride ion-yielding materials can be employed as sources of soluble fluoride in the present compositions. Examples of suitable fluoride ion-yielding materials are found in U.S. Pat. No. 3,535,421, Oct. 20, 1970 to Briner et al. and U.S. Pat. No. 3,678,154, Jul. 18, 1982 to Widder et al., both being incorporated herein by reference. Representative fluoride ion sources include: stannous fluoride, sodium fluoride, potassium fluoride, sodium monofluorophosphate and many others. Stannous fluoride and sodium fluoride are particularly preferred, as well as mixtures thereof.

Water is also present in the toothpastes of this invention. Water employed in the preparation of commercially suitable toothpastes should preferably be aleionized and free of organic impurities. Water generally comprises from about 10% to 50% preferably from about 20% to 40%, by weight of the toothpaste compositions herein. These amounts of water include the free water which is added plus that which is introduced with other materials such as with sorbitol.

In preparing toothpastes, it is necessary to add some thickening material to provide a desirable consistency. Preferred thickening agents are carboxynyl polymers, carrageenan, hydroxethyl cellulose and water soluble salts of cellulose ethers such as sodium carboxymethyl cellulose and sodium carboxymethyl hydroxethyl cellulose. Natural bums such as gum karaya, xanthan gum, gum arabic, and gum tragacanth can also be used. Thickening agents in an amount from 0.5% to 5.0% by weight of the total composition can be used.

It is also desirable to include some humectant material in a toothpaste to keep it from hardening. Suitable humectants include glycerin, sorbitol, and other edible polyhydric alcohols at a level of from about 15% to about 70%.

Also desirable for inclusion in the compositions of the present invention are other stannous salts such as stannous pyrophosphate and stannous gluconate and antimicrobials such as quaternary ammonium salts, such as cetyl pyridinium chloride and tetradecylethyl pyridinium chloride, bis-biquanide salts, copper bisglycinate, nonionic anti microbial salts and flavor oils. Also useful are enzymes, including endoglycosidase, papain, dextranase, mutanase and mixtures thereof. Such agents are disclosed in U.S. Pat. No. 2,946,725, Jul. 26, 1960, to Norris et al. and U.S. Pat. No. 4,051,234, Sep. 27, 1977 to Gieske et al., incorporated herein by reference. Other optional components include buffering agents, bicarbonates, peroxides, nitrate salts such as sodium and potassium nitrate. These agents, if present, are included at levels of from about 0.01% to about 30%.

Another preferred embodiment of the present invention is a mouthwash composition. Mouthwashes generally comprise from about 20:1 to about 2:1 of a water/ethyl alcohol solution and preferably other ingredients such as flavor, sweeteners, humectants, such as glycerin and sorbitol give a moist feel to the mouth. Generally, on a weight basis the mouthwashes of the invention comprise 5% to 60% (preferably 10% to 20%) ethyl alcohol, 0% to 20% (preferably 5% to 20%) of a humectant, 0% to 2% (preferably 0.01% to 0.15%) emulsifying agent, 0% to 0.5% (preferably 0.005% to 0.06%) sweetening agent such as saccharin, 0% to 0.3% (preferably 0.03% to 0.3%) flavoring agent, and the balance water. The amount of antimicrobial agent in mouthwashes is typically from about 0.01% to about 1.5% by weight.

Suitable lozenge and chewing gum components are disclosed in U.S. Pat. No. 4,083,955, Apr. 11, 1978 to Grabenstetter et al., incorporated herein by reference The following examples further describe and demonstrate preferred embodiments within the scope of the present invention. The examples are given solely for illustration and are not to be construed as limitations of this invention as many variations are possible without departing from the spirit and scope thereof.

EXAMPLE I

A dentifrice composition of the present invention contains the following components as described below.

| Component | Wgt % |
|---|---|
| Sorbitol 70% soln | 24.200% |
| RO Water | 24.757% |
| Glycerin | 7.000% |
| Carboxymethyl Cellulose | 0.500% |
| PEG 6 | 4.000% |
| Sodium Fluoride | 0.243% |
| Sodium Saccharine | 0.130% |
| Monosodium Phosphate | 0.415% |
| Trisodium Phosphate | 0.395% |
| Sodium Tartrate | 1.000% |
| TiO2 | 0.500% |
| Silica | 35.000% |
| Sodium Lauroyl Sarcosinate (95% active) | 1.060% |
| Flavor | 0.800% |

*Carboxyvinyl polymer supplied by B.F. Goodrich Company as Carbomer 956.

The jacket temperature of a mixing tank is set to about 150° F. (65° C.) to about 160° F. (71° C.). The humectants and water are added to the mixing tank and agitation is started. When the temperature reaches approximately 120° F. (50° C.) fluoride, sweetening agents, buffering agents, chelant, coloring agents and titanium dioxide are added. Thickening agents are added to the abrasive and the resulting mixture is added to the mixing tank with high agitation. The surfactant is added to the combination and mixing is continued. The tank is cooled to 120° F. (50° C.) and the flavoring agents are added. Mixing is continued for approximately 5 minutes.

| Component | Ex. II Wgt % | Ex. III Wgt % | Ex. IV Wgt % |
|---|---|---|---|
| Sorbitol 70% soln | 28.100 | 24.750 | 24.100 |
| RO Water | 22.177 | 19.496 | 18.329 |
| Glycerin | 7.000 | 10.000 | 9.000 |
| Carboxymethyl Cellulose | 0.600 | 0.800 | 0.900 |
| PEG 6 | 4.000 | 3.000 | 3.000 |
| Sodium Fluoride | 0.243 | 0.243 | 0.243 |
| Sodium Saccharine | 0.130 | 0.460 | 0.460 |
| Monosodium Phosphate | 0.415 | — | — |
| Trisodium Phosphate | 0.395 | — | — |
| Sodium Tartrate | 1.000 | 1.000 | 1.000 |
| Cocoamidopropyl betaine (30% solution) | 2.000 | — | 2.667 |
| TiO2 | 0.500 | — | — |

-continued

| Component | Ex. II Wgt % | Ex. III Wgt % | Ex. IV Wgt % |
|---|---|---|---|
| Silica | 32.000 | 30.000 | 30.000 |
| Sodium Lauroyl Sarcosinate (95% active) | 0.640 | 1.060 | 1.060 |
| Sodium Acid Pyrophosphate | — | 1.221 | 1.221 |
| Tetra Sodium Pyrophosphate | — | 0.660 | 0.660 |
| Tetra Potassium Pyrphosphate (60% soln) | — | 6.060 | 6.060 |
| Color, FD&C Blue (1%) | — | 0.400 | 0.400 |
| Flavor | 0.800 | 0.850 | 0.900 |

Examples V–VIII rinse, lozenge and chewing gum examples of the present invention.

| Component | Weight % | |
|---|---|---|
| | Example V | Example VI |
| Undenatured Alcohol | 16.250 | 16.250 |
| Glycerine | 10.000 | 10.000 |
| Sodium Lauroyl Sarcosinate | 0.100 | 0.080 |
| Sodium Tartrate | 0.500 | 1.000 |
| Cocoamidopropylbetaine | — | 0.060 |
| Saccharin | 0.060 | 0.060 |
| Flavor | 0.150 | 0.120 |
| Water | 72.940 | 72.430 |

EXAMPLE VII

| Component | Weight % |
|---|---|
| Sorbitol | 17.500 |
| Mannitol | 17.500 |
| Sodium Lauroyl Sarcosinate | 0.050 |
| Sodium Tartrate | 0.200 |
| Saccharin | 0.250 |
| Flavor | 1.500 |
| Corn Syrup | Balance |

EXAMPLE VIII

| Component | Weight % |
|---|---|
| Gum Base<br>30 parts Estergum<br>45 parts Coumorone Resin<br>15 parts Dry Latex | 30.000 |
| Sugar | 50.000 |
| Corn Syrup | 18.175 |
| Sodium Lauroyl Sarcosinate | 0.075 |
| Sodium Tartrate | 0.250 |
| Flavor | 1.500 |

In the above examples, substantially similar results are obtained when the surfactant(s), chelating agents(s) and combinations thereof are substituted with other similar components herein disclosed and described.

What is claimed is:

1. An oral composition providing improved oral cleansing with reduced desquamation comprising:
   a. from about 0.1% to about 2.5% of an isethionate surfactant;
   b. from about 0.1% to about 2.5% of tartaric acid and pharmaceutically-acceptable salts thereof;
   c. an amphoteric betaine surfactant selected from the group consisting of decylbetaine, cocobetaine, myristylbetaine, palmitylbetaine, laurylbetaine, cetylbetaine, stearylbetaine, cocobetaine/cocamine oxide, cocamidoethyl betaine, cocoamidopropyl betaine, cocoamidopropyl hydroxysultaine, lauramidopropyl betaine, rincinoleicamidobetaine and mixtures thereof;
   d. an enzyme selected from the group consisting of endoglycosidase, papain, dextranase, mutanase, and mixtures thereof; and
   e. a fluoride ion source selected from the group consisting of sodium fluoride, stannous fluoride, sodium monofluorophosphate, potassium fluoride and mixtures thereof;

wherein the level of a. and b. does not exceed 4.0% by weight of the total composition and further wherein said composition is substantially free of copper, iron, and zinc ions.

2. An oral composition according to claim 1 wherein said tartaric acid salt is selected from the group consisting of sodium tartrate, potassium tartrate, sodium potassium tartrate, and mixtures thereof.

3. An oral composition according to claim 2 further comprising from about 0.1% to about 2.5% of an additional chelating agent selected from the group consisting of citric acid and alkali metal titrates and mixtures thereof.

4. An oral composition according to claim 3 wherein said amphoteric betaine surfactant is cocoamid opropyl-betaine.

5. An oral composition according to claim 4 wherein the fluoride ion source is sodium fluoride.

6. An oral composition according to claim 5 further comprising an abrasive.

7. An oral composition according to claim 6 wherein the enzyme is endoglycosidase.

8. An oral composition according to claim 7 further comprising from about 15% to about 70% of a humectant selected from among the group consisting of glycerin, sorbitol, propylene glycol and mixtures thereof.

9. A method for preventing and treating plaque and gingivitis with reduced desquamation comprising the application of a safe and effective amount of a composition according to claim 1, to the teeth and other oral surfaces.

10. A method for preventing and treating plaque and gingivitis with reduced desquamation comprising the application of a safe and effective amount of a composition according to claim 3, to the teeth and other oral surfaces.

11. A method for preventing and treating plaque and gingivitis with reduced desquamation comprising the application of a safe and effective amount of a composition according to claim 8, to the teeth and other oral surfaces.

* * * * *